(12) United States Patent
Roth

(10) Patent No.: US 10,115,188 B2
(45) Date of Patent: Oct. 30, 2018

(54) POROUS MATERIAL ANALYSIS SYSTEM AND METHOD FOR HYDROLOGY, PETROLEUM AND ENVIRONMENT ENGINEERING

(71) Applicant: IROCK TECHNOLOGIES CO., LTD., Beijing (CN)

(72) Inventor: Sven Roth, Beijing (CN)

(73) Assignee: IROCK TECHNOLOGIES CO., LTD., Beijing (CN)

( * ) Notice: Subject to any disclaimer, the term of this patent is extended or adjusted under 35 U.S.C. 154(b) by 45 days.

(21) Appl. No.: 15/410,734

(22) Filed: Jan. 19, 2017

(65) Prior Publication Data

US 2017/0132781 A1    May 11, 2017

Related U.S. Application Data

(63) Continuation of application No. PCT/CN2015/089409, filed on Sep. 11, 2015.

(51) Int. Cl.
*G06K 9/00* (2006.01)
*G06T 7/00* (2017.01)
(Continued)

(52) U.S. Cl.
CPC .......... *G06T 7/0004* (2013.01); *G01N 15/08* (2013.01); *G01N 15/0806* (2013.01); *G01N 23/046* (2013.01); *G06K 9/4638* (2013.01); *G06T 7/97* (2017.01); *G01N 15/088* (2013.01); *G01N 2015/0846* (2013.01); *G01N 2223/616* (2013.01); *G01N 2223/649* (2013.01); *G06T 2207/10012* (2013.01); *G06T 2207/10081* (2013.01); *G06T 2207/30181* (2013.01)

(58) Field of Classification Search
None
See application file for complete search history.

(56) References Cited

U.S. PATENT DOCUMENTS

2012/0221306 A1    8/2012  Hurley
2012/0281883 A1*  11/2012  Hurley ............... G01N 21/6458
                                                          382/109

OTHER PUBLICATIONS

Susanne Hemes, Guillaume Desbois, Janos L. Urai, Birgit Schroppel, Jens-Oliver Schwarzi Microporous and Mesoporous Materials—Multi-scale characterization of porosity in Boom Clay (HADES-level, Mol, Belgium) using a combination of X-ray m-CT, 2D BIB-SEM and FIB-SEM tomography) vol. 208, May 15, 2015, pp. 1-20.*

(Continued)

*Primary Examiner* — Idowu O Osifade
(74) *Attorney, Agent, or Firm* — Syncoda LLC; Feng Ma; Junjie Feng

(57) ABSTRACT

A computer-implemented method for deriving properties of a porous material, the method includes: a first stage including: obtaining a first image of the porous material on a first scale; extracting a first network of pores from the first image; and deriving a first set of properties of the porous material using a first network flow modeling based on the first network; and a second stage including: obtaining a second image of the porous material on a second scale larger than the first scale; extracting a second network of pores from the second image; and deriving a second set of properties of the porous material using a second network flow modeling based on the second network and the first set of properties.

20 Claims, 11 Drawing Sheets

(51) Int. Cl.
*G01N 15/08* (2006.01)
*G01N 23/046* (2018.01)
*G06K 9/46* (2006.01)

(56) References Cited

OTHER PUBLICATIONS

International Search Report and Written Opinion dated Jun. 20, 2016 in PCT/CN2015/089409.
Yao, Jun et al., Upscaling of Carbonate Rocks From Micropore Scale to Core Scale, Journal for Multiscale Computational Engineering, 11 (5): 497-504 (2013).

* cited by examiner

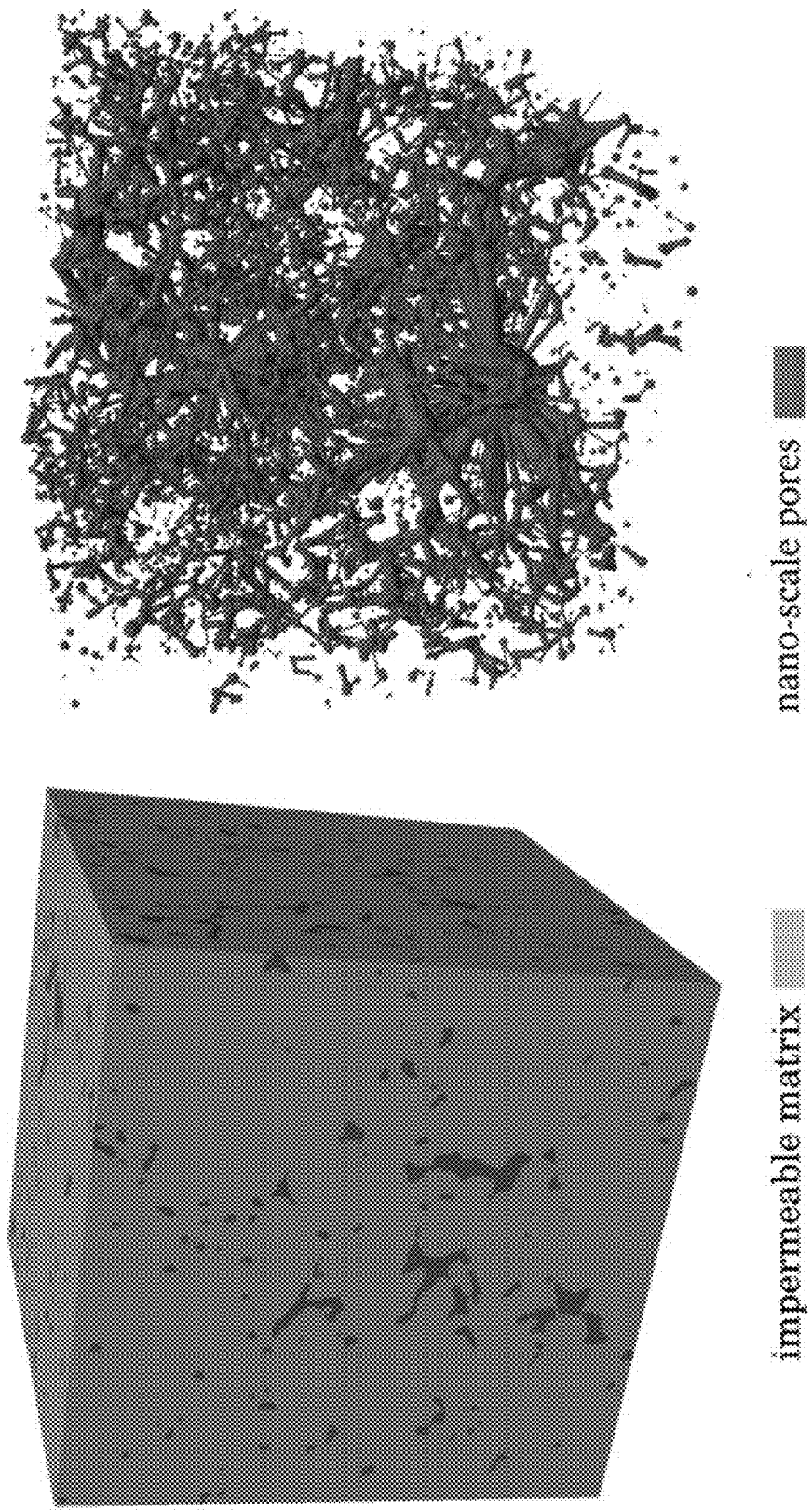

POROUS MATERIAL ANALYSIS SYSTEM AND METHOD FOR HYDROLOGY, PETROLEUM AND ENVIRONMENT ENGINEERING

CROSS-REFERENCE TO RELATED APPLICATION

The present application is a continuation of, and claims priority to, PCT/CN2015/089409 filed on Sep. 11, 2015, the disclosure of which is hereby incorporated by reference in its entirety.

BACKGROUND

Studying the structures and petrophysical properties of porous materials such as porous rocks can be useful in hydrology, petroleum engineering, and environment engineering.

SUMMARY

In an aspect, pore-network modeling is employed to predict petrophysical properties of porous media. The pore-network modeling can be based on micro-X-ray computerized tomography (whole core CT, micro-CT and nano-CT) scans, focused ion beam scanning electron microscope (FIB-SEM images), and any other 3D imaging of a rock sample, which can be a few micrometers to decimeters across. The CT images can then be segmented into void-spaces and solid matrices, which can be modeled as a network including a number of pores (e.g., larger void spaces) connected by throats (e.g., narrower channels). Flow simulations can then be performed on the extracted network, with parameterized geometries and topology, to predict its single-phase and two-phase flow properties for fluids flowing therethrough. Macroscopic properties such as capillary pressure and relative permeability can be determined for the network.

Some types of rocks, such as shale, tight sands, and carbonate rocks, can have a wide range of pore sizes. As such, it may be difficult to take 3D images of these rocks and capture a whole range of scales, for example from nano meter pores to vugs. As a result, it may be difficult to predict the flow properties of these unconventional rocks using conventional methods.

Embodiments disclosed herein provide systems and methods including a multi-scale workflow that is capable of predicting single and multi-phase flow properties of heterogeneous and complex rocks.

According to some embodiments, upscaling is employed to interpret data acquired on small rock samples, such as core plugs or smaller, and use such data as input to a much larger scale, such as reservoir modeling and simulations. The simulation results can be used, for example, in the estimation of hydrocarbon content in a reservoir, and in turn for hydrocarbon exploration and extraction planning, etc.

In an example workflow described in detail below, multi-scale images of the rock can be obtained, and can be analyzed at the different scales. The results can then be combined using a multi-scale network flow simulator.

Embodiments disclosed herein provide methods, systems, and computer software configured to predict petrophysical properties of rock based on X-ray CT images of porous media, where the rock pore spaces can have large variations. For samples with some pore spaces smaller than the resolution of the X-ray CT images, micron-level X-ray imaging can be combined with imaging of a higher resolution, such as nano-X-ray CT or electron microscopy.

Various petrophysical properties of porous media, such as porosity, absolute permeability, formation resistivity factor, capillary pressure curves, relative permeability curves, resistivity index, etc., can thus be determined from the 3D images.

Porous rocks may contain a wide range of pore sizes which may be difficult to capture in a single image. For example, carbonate reservoir rocks and unconventional reservoir rocks such as shales and tight sands are such rocks that contain pores with large variations in sizes.

According to some embodiments, a porous rock sample is scanned at different scales. On a smaller scale, a rock sample around 0.05-0.1 mm across can be scanned with a resolution of about 10 nm; on a larger scale, whole cores, several cm in extent can be scanned with a resolution of around 0.1 mm. The scans can be performed using various types of physical signals and tools, such as using X-ray or FIB-SEM.

For example, on the smaller scale, in a process referred to as the upscaling stage 1, a nano-scale image can then be segmented into different types of elements, such as two types of elements labeled with void spaces, and solid matrices, respectively. The petrophysical properties of the nano-scale image can then be obtained by extracting a network and performing flow simulations. In some example implementations, the porous medium is scanned on a sale of about 50 microns to about 100 microns, at a resolution of about 1 nm to about 50 nm, for example.

In a process referred to as the upscaling stage 2, an X-ray micro-CT scan, for example with a resolution of one micron or better, can be performed on a sample of porous medium having a dimension of a few mm across. The CT images can be segmented into, for example, three types of elements and labeled with, for example: (a) void-spaces, (b) voxels that contain nano-scale pores, and (c) impermeable solid matrices. Based on these, the properties of the micro-scale porosity network can be extracted, and at the same time the properties of the nano-scale porosity system can be incorporated. In some example implementations, the porous medium is scanned on a scale of about 100 microns to about 10 mm, at a resolution of about 50 nm to about 1 micron, for example.

In an upscaling stage 3, a macro-level X-ray CT with a resolution of, for example, several microns, can be performed on a larger sample, such several cm across (typically a core plug or whole core). The CT images can be segmented into, for example, three types of elements labeled respectively with: (a) void-spaces, (b) voxels that contain micro-scale pores (which already include the nano-scale pores), and (c) impermeable solid matrices. Properties of the macro-scale porosity network (vugs) can then be extracted, and at the same time the combined properties of the nano-scale and the micro-scale (obtained during the upscaling stage 2) porosity systems can be incorporated. In some example implementations, the porous medium is scanned on a scale of about 1 cm to about 20 cm, at a resolution of about 1 micron to about 100 microns, for example.

The procedures can be repeated in higher upscaling stages to upscale the combined nano+micro+macro-scale properties to a whole reservoir core level.

Embodiments disclosed herein are therefore not restricted by size ranges. As such, the same stage-wise approach can be applied to entire formations and reservoirs. Although various embodiments use a three-stage upscaling process as an illustration, it is understood that the multi-stage upscaling process according to the embodiments disclosed herein are not limited to three stages, but instead can have 2, 4, 5, or more stages.

In some embodiments, a generalized network extraction algorithm for processing multi-label images is provided.

In some embodiments, a generalized network flow simulation method is provided for handling sub-resolution porous elements together with void elements (pores and throats).

Applications of the methods for predicting petrophysical properties may include deriving one or more of: capillary pressure curves, relative permeability curves, resistivity index, scanning curves for capillary pressure, relative permeability, and resistivity index.

Applications of the method for predicting the wettability index of the rock sample for any given distributions of contact angles may include, for example, the Amott-Harvey index, as well as the USBM wettability index.

The upscaling workflow may apply to different numbers of upscaling stages, such as 2-stage, 3-stage, 4-stage and beyond (unlimited scale range), where the inputs of the model in one of the stages can be a multi-labeled 3D image of the porous media.

The workflow can be used for predicting drainage as well as imbibition cycles and subsequent flooding cycles.

The present disclosure provides a first capillary-pressure-dominated upscaling work flow comprising unlimited scale ranges, and the work flow is based on sound physical principles of capillary equilibrium.

Various embodiments disclosed herein also provide a first physically correct, capillary pressure dominated flow simulator to upscale single-phase (total porosity, absolute permeability, formation resistivity factor) and two-phase flow properties (relative permeability, resistivity index, Amott-Harvey index, USBM wettability index) to core plug, whole core, facies, formations or reservoirs.

Other aspects and advantages of the claimed embodiments will become apparent from the following description and the attached claims.

BRIEF DESCRIPTION OF THE DRAWINGS

FIG. 2B illustrates the processed and segmented nano-level model and the extracted network of the upscaling stage 1.

DETAILED DESCRIPTION

Embodiments are described in detail below with respect to the drawings. In one aspect, some embodiments disclosed herein relate to a method, system, and computer software configured to determine petrophysical properties of porous rocks based on sample X-ray CT images, where the rock pore spaces have a wide distribution in sizes, some of which can be smaller than the resolution of the X-ray CT images.

The CT scanning can be micro-CT scanning of samples with a size of about a few millimeters. The resolution of the scan can be, for example, submicron or a few microns.

Figure 1:
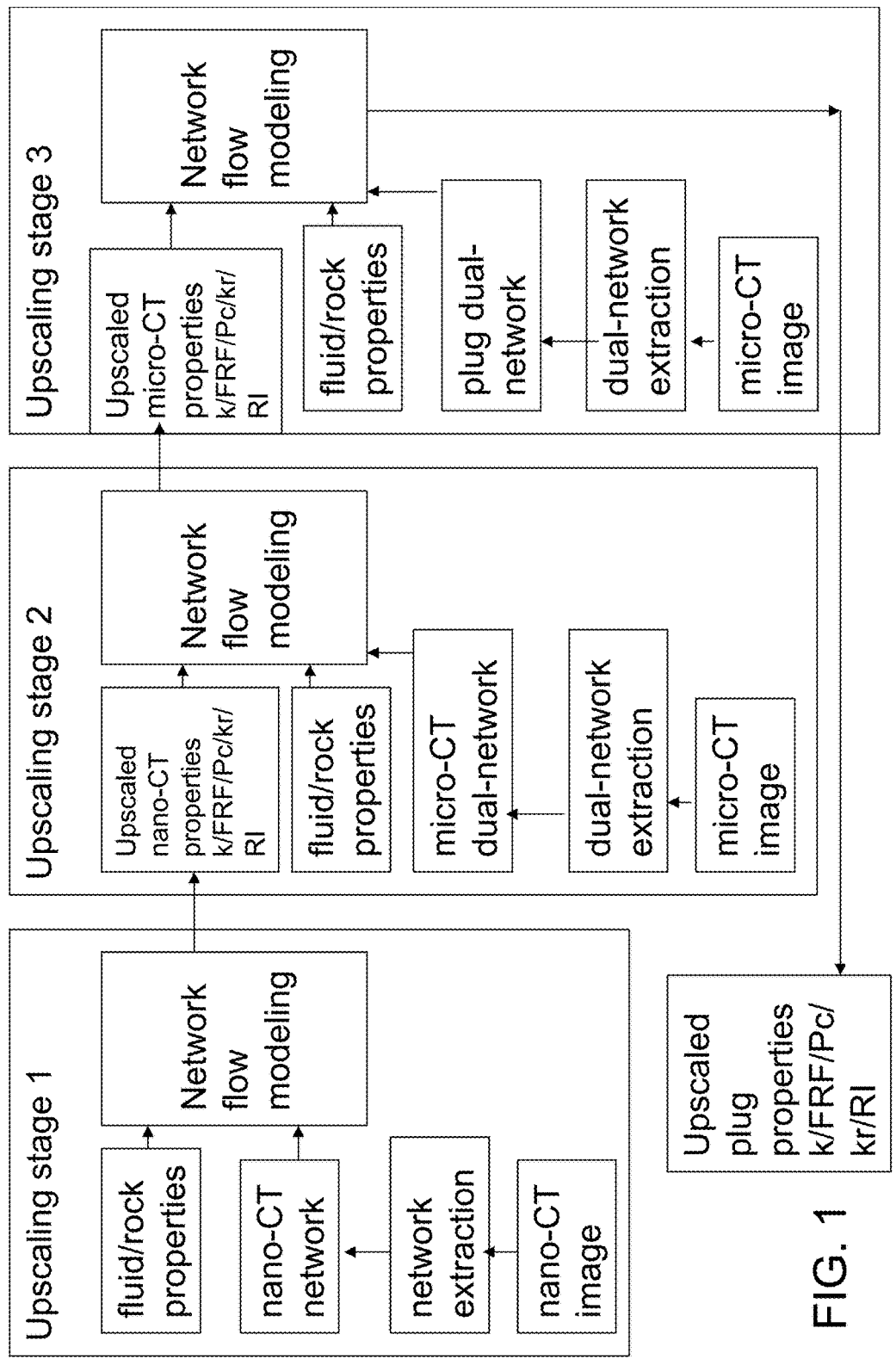
FIG. 1 is a schematic diagram of an upscaling workflow.

Although the imaging of the rock and upscaling of the results can be performed in one, two, three or more upscaling stages, in the following the imaging of the rock samples and upscaling of the flow properties are demonstrated using a three-stage approach, as illustrated in FIG. 1.

Upscaling Stage 1

Figure 2A:
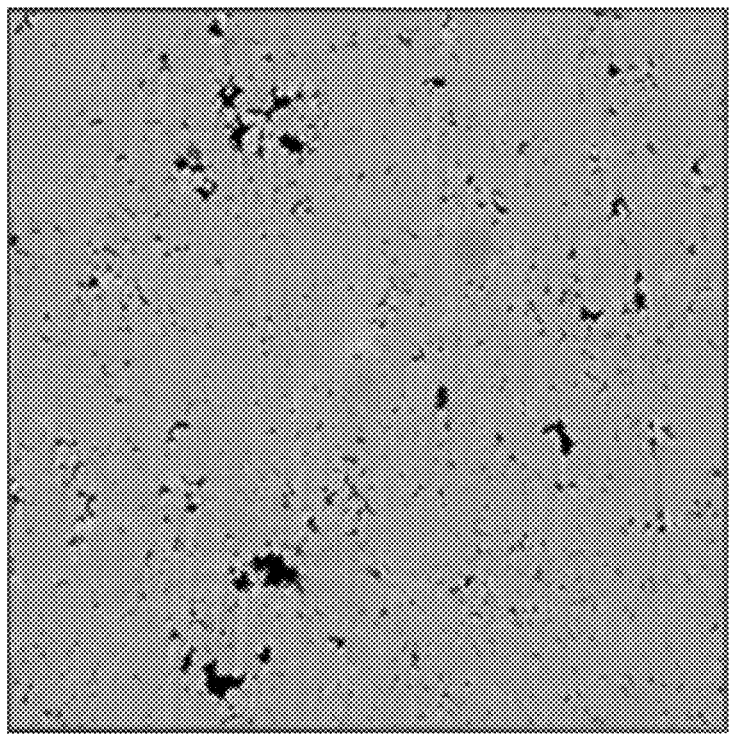
FIG. 2A illustrates sample grey-scale nano-level X-ray CT images of the upscaling stage 1.
Figure 2A:
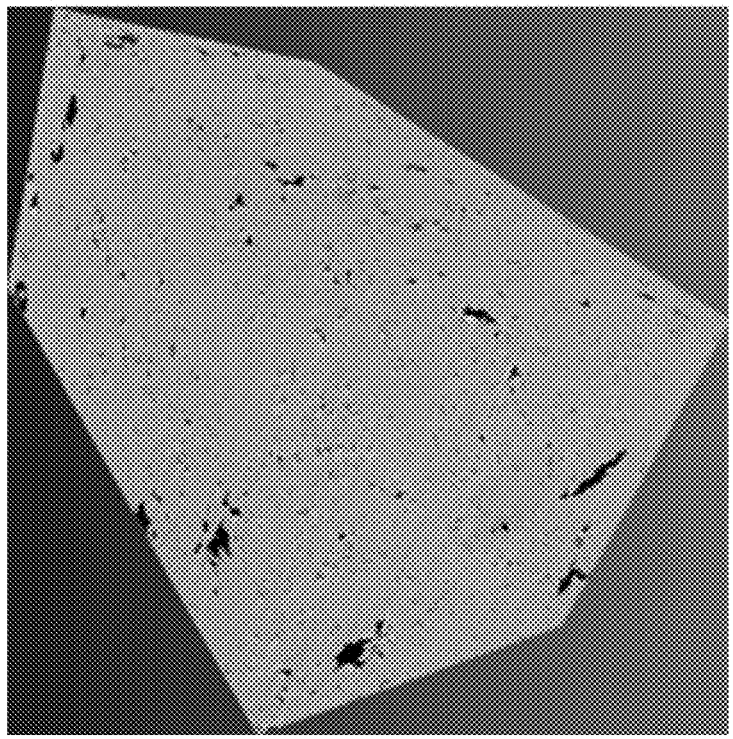

Nano-CT images are obtained from the regions of the rock samples containing nano-porosity. FIG. 2A illustrates sample grey-scale nano-level X-ray CT images in the upscaling stage 1.

The images are then segmented to voids (such as nano-scale pores), and solid voxels (such as impermeable matrices). A computer-implemented network extraction software can be used to extract the network from the void voxels. FIG. 2B illustrates the processed and segmented nano-level model and the extracted network of the upscaling stage 1.

A two-phase flow modeling software can be used to determine the single-phase properties (including for example the absolute permeability and formation resistivity factor), and two-phase flow properties (including for example a capillary pressure curve, relative permeability, and resistivity index) of the network of nano-scale pores, referred to as the nano-CT network. Some basic fluid/rock properties can be used as input to the network flow modeling, including for example density, viscosity, and resistivity of the individual fluids, as well as interfacial tension (IFT) between the fluids, and fluid-pore surface contact angles.

An example two-phase flow network modeling code is described in P. H. Valvatne and M. J. Blunt, "Predictive pore-scale modeling of two-phase flow in mixed wet media," Water Resources Research, 40, W07406, the disclosure of which is hereby incorporated by reference in its entirety.

Figure 2C:
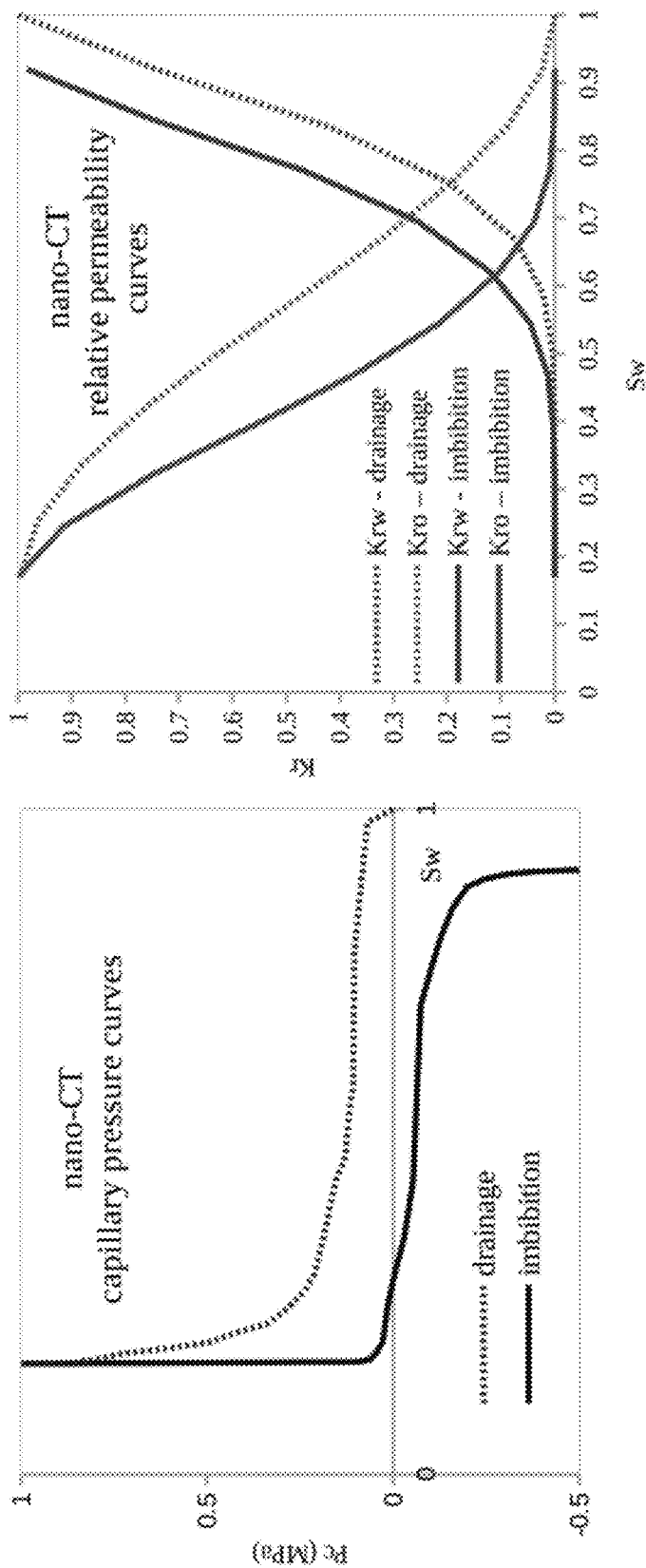
FIG. 2C illustrates the upscaling results of the upscaling stage 1.

FIG. 2C illustrates some example upscaling results of the upscaling stage 1, including the nano-CT capillary pressure curves for drainage and imbibition, and nano-CT relative permeability curves for drainage and imbibition.

Upscaling Stage 2

As illustrated in FIG. 1, the results from the network flow modeling in the upscaling stage 1 can be used as input to the network flow modeling in the upscaling stage 2. The upscaled nano-CT properties may include, for example, absolute permeability (k), capillary pressure (Pc), relative permeability (kr), and resistivity index (RI).

Figure 3A:
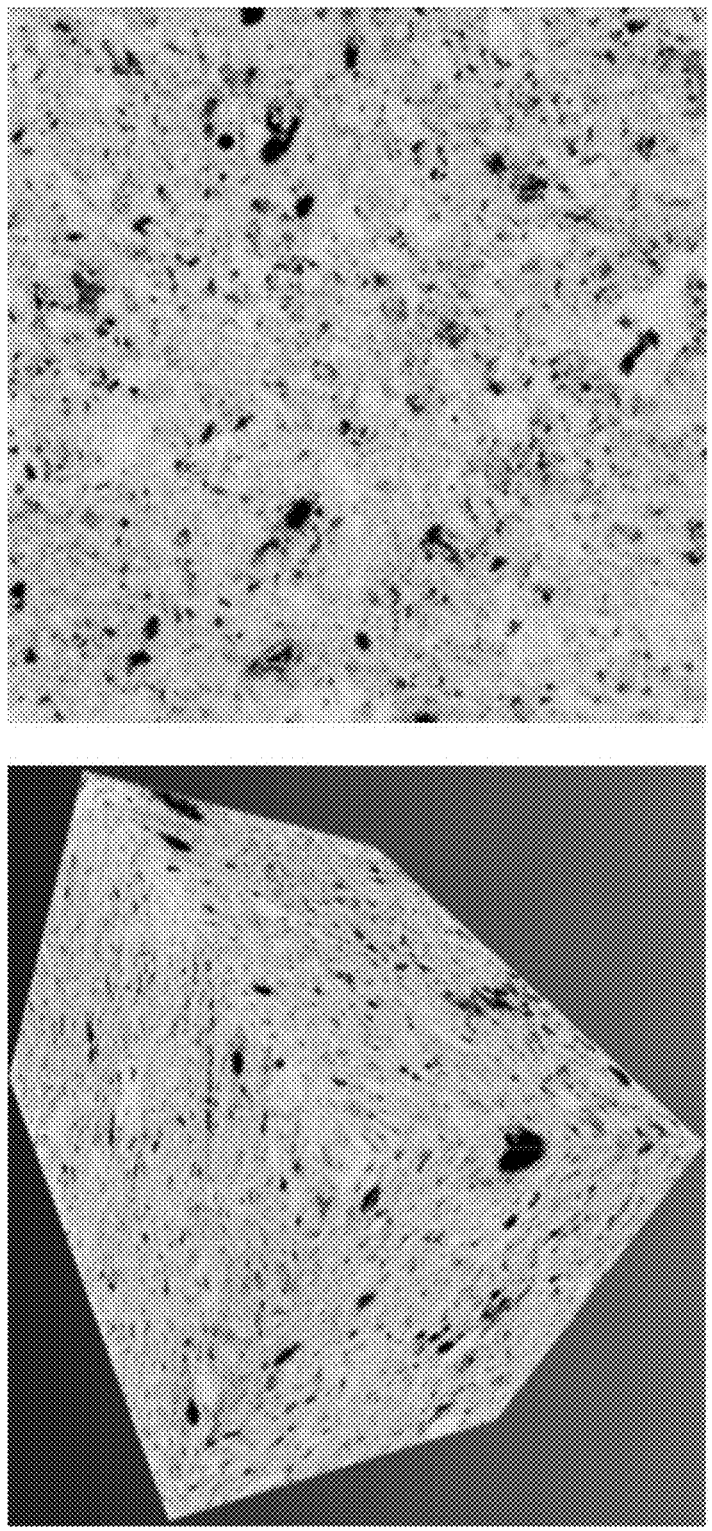
FIG. 3A illustrates sample grey-scale X-ray micro-CT images of the upscaling stage 2.

In the upscaling stage 2, more images of the rock can be acquired using micro-CT scanning FIG. 3A illustrates sample grey-scale X-ray micro-CT images in the upscaling stage 2.

Figure 3B:
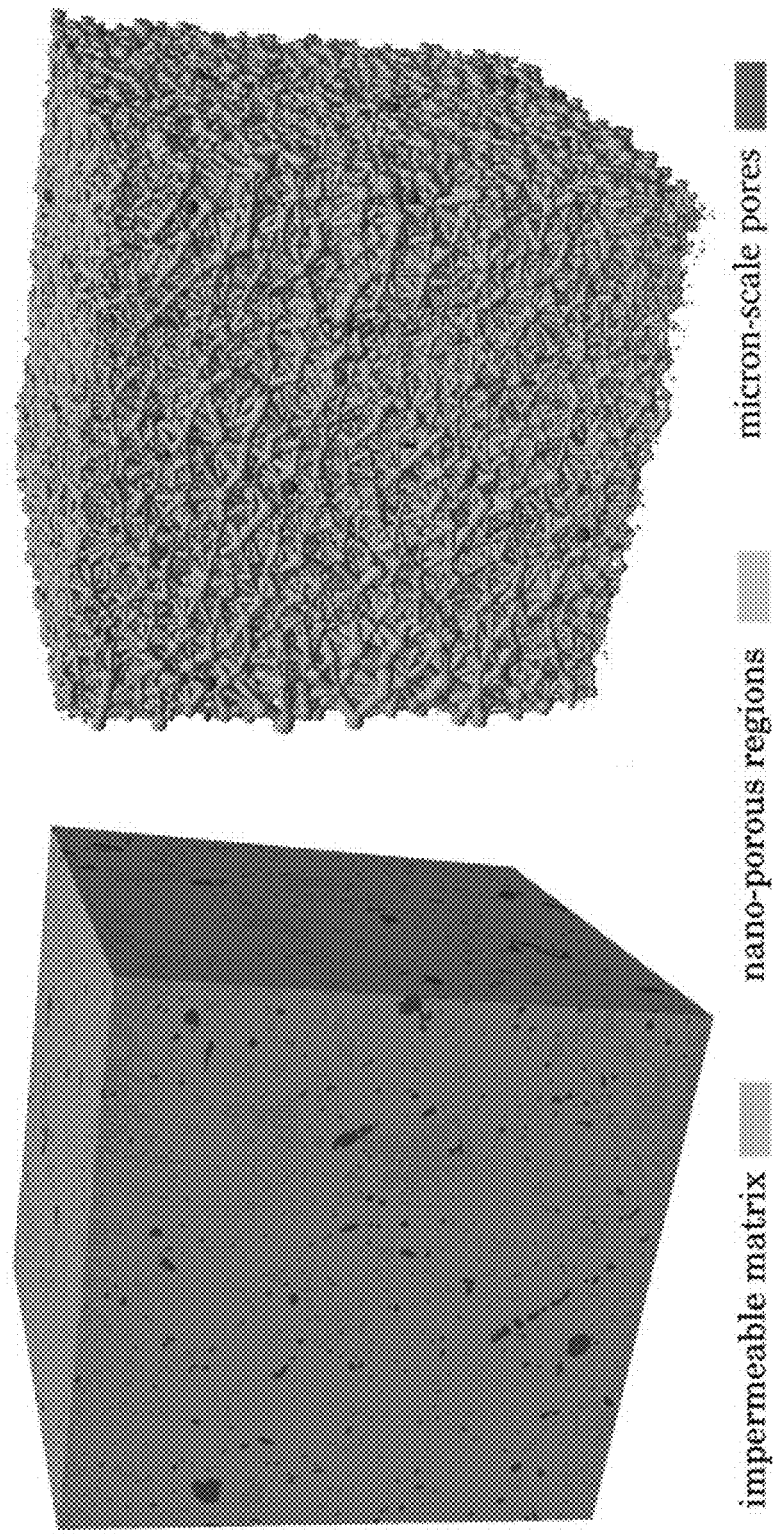
FIG. 3B illustrates the processed and segmented micro-CT model and the extracted network of the upscaling stage 2.

The voxels can then be segmented into different types labeled with, for example: solid voxels, pore voxels, and voxels containing nano-scale pores (referred to as nano-porosity). FIG. 3B illustrates the processed and segmented micro-CT model and the extracted network of the upscaling stage 2, including impermeable matrices, nano-porous regions, and micro-scale pores. In some implementations, the volume of the nano-porous region can be extracted from the micro-CT, while the data/information of the nano pores can be obtained from the nano-CT with higher resolutions.

Embodiments disclosed herein provide a method configured to extract a network of the pore spaces combined with the nano-porosity blocks, referred to as the dual-network extraction.

The pores, throats, and the nano-porosity blocks as part of the combined network can be referred to as "elements." The pore elements detected at this scale may be referred to as macro-pores, as compared with the nano-scale pores detected in the upscaling stage 1. Various algorithms can be employed to generate the network of the macro-pore elements. One example of such network extraction algorithms is described in H. Dong, M. J. Blunt. "Pore-network extraction from micro-computerized-tomography images", Physical Review E, 80(3):036307, (2009), the disclosure of which is hereby incorporated by reference in its entirety.

The nano-porosity elements can be generated using, for example, the maximal ball algorithm, but the elements can be limited in their sizes to facilitate accurate computation of flow properties. In some embodiments, a maximum size of 15 voxels across is found to be a good compromise between the speed of the flow modeling computations and the accuracy of the calculations. The nano-porosity elements generated in this manner can be considered as a finite volume mesh that are combined with the network of the macro-pores.

The extracted micro-CT dual-network, together with the basic fluid/rock properties and the upscaled nano-CT properties can be used as inputs to a network flow modeling of the upscaling stage 2.

The two-phase flow modeling code by Valvatne and Blunt (2004) can be extended to model the flow through the combined network. In this approach the flow through the pore elements can be described using the equations as discussed in Valvatne and Blunt (2004).

The flow through the nano-porosity elements, however, can be described using the multi-phase Darcy law with the flow properties obtained from the upscaling stage 1. The network model works by gradually increasing the oil pressure in oil-injection cycles and decreasing it in the water-injection cycle, which is similar to what is used in the experimental measurements.

The water-saturation, the flow, and the electrical conductivity of the nano-porosity elements can be calculated from the capillary pressure curve, the relative permeability, and the resistivity indices, respectively, as obtained in the upscaling stage 1. The flow equations for the combined network of the pore and nano-porosity elements are put together using the mass conservation equation as discussed in Valvatne and Blunt (2004) and solved to obtain the single and two-phase flow properties for the micro-CT images.

Figure 3C:
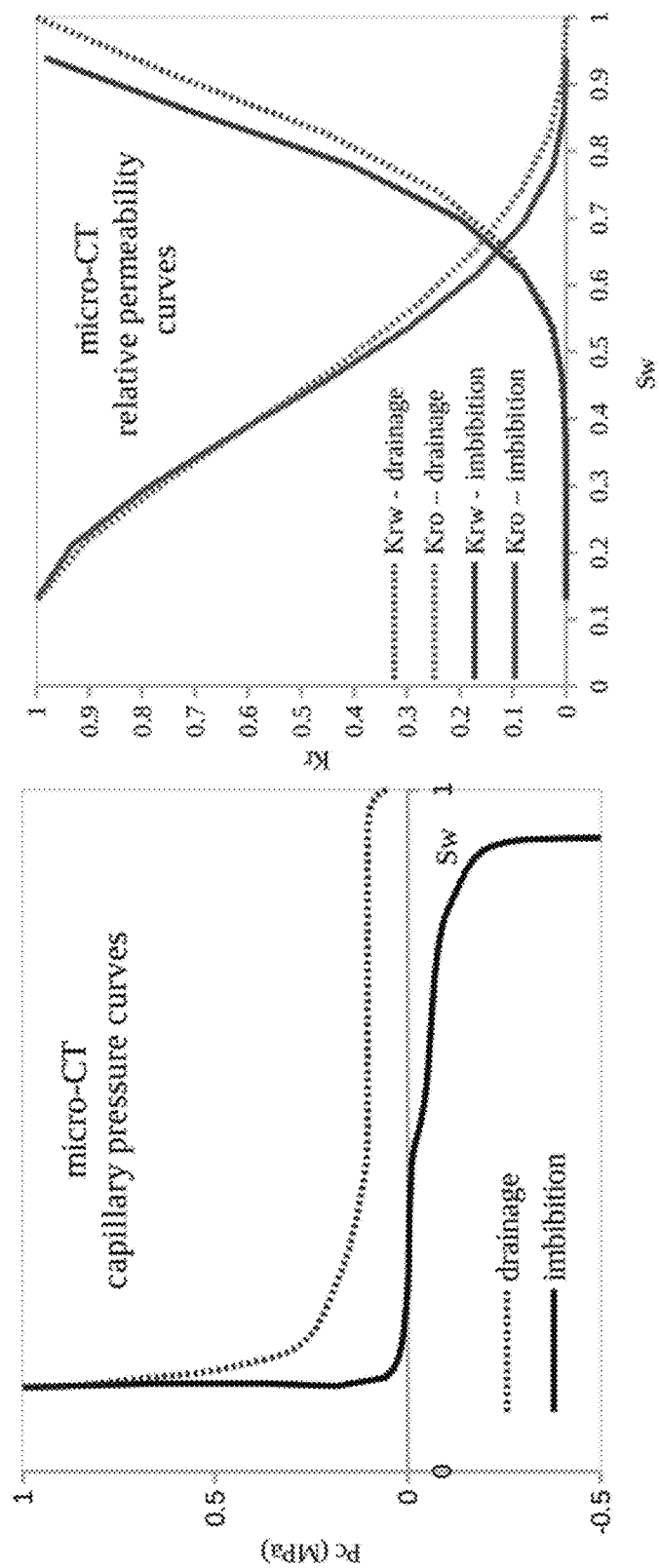
FIG. 3C illustrates the upscaling results of the upscaling stage 2.

FIG. 3C illustrates some example upscaling results of the upscaling stage 2, including micro-CT capillary pressure curves for drainage and imbibition, and micro-CT relative permeability curves for drainage and imbibition.

Upscaling Stage 3

As illustrated in FIG. 1, the results from the network flow modeling in the upscaling stage 2 can be used as input to the network flow modeling in the upscaling stage 3. The upscaled micro-CT properties may include, for example, absolute permeability (k), capillary pressure (Pc), relative permeability (kr), and resistivity index (RI).

In the upscaling stage 3, more images of the rock can be acquired using the plug or whole-core micro-CT imaging. The CT scanner can be a micro-CT scanner or a whole-core scanner with a larger scanning volume.

In the case that the rock sample has large void spaces (vuggy porosity), which cannot be captured at the micro-CT level (properties calculated on smaller-scale images are not necessarily representative for the entire rock sample), images of the rock can be acquired using CT scanning with larger voxel sizes.

Figure 4A:
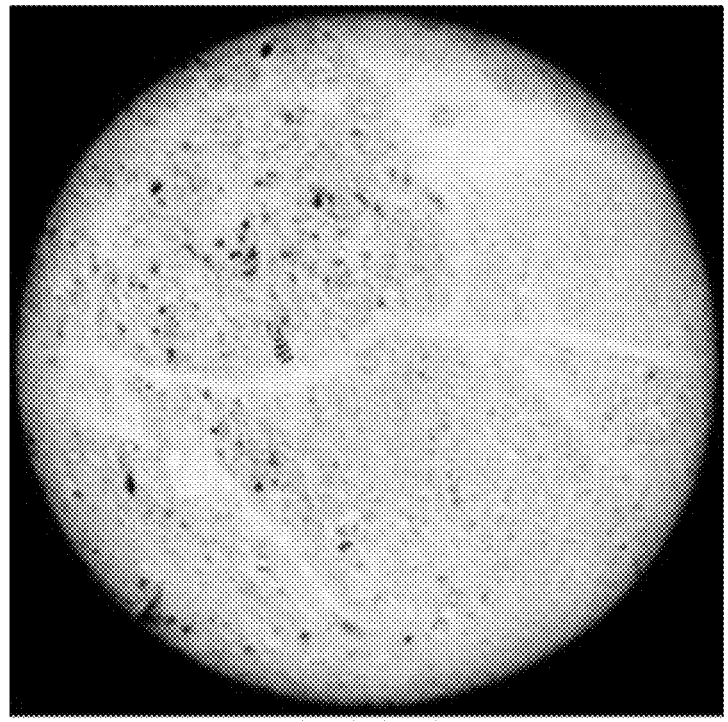
FIG. 4A illustrates sample grey-scale X-ray core-plug-level CT images of upscaling stage 3.
Figure 4A:
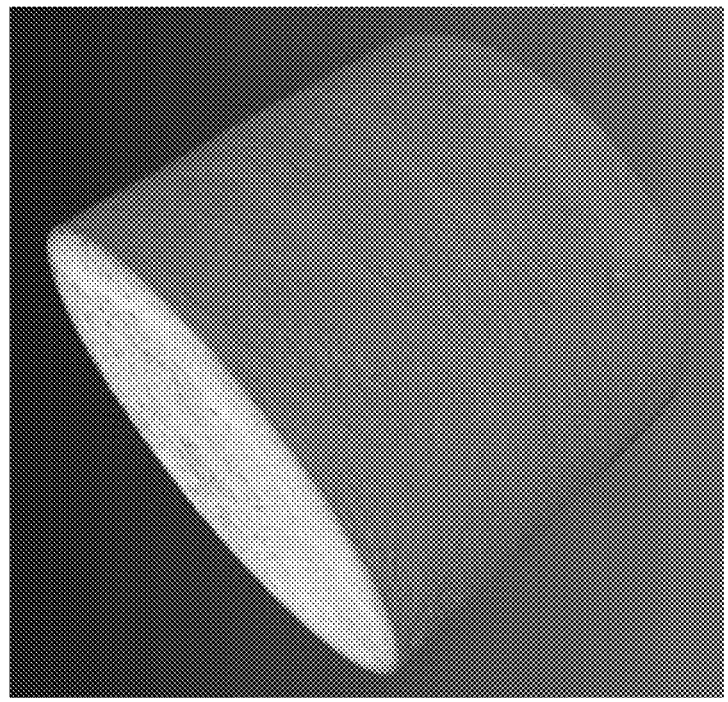

The voxels obtained with the larger CT images can be segmented into three labels: solid voxels, void voxels (vugs), and voxels that contain micro- and nano-scale pores (referred to as micro-CT). FIG. 4A illustrates sample greyscale X-ray core-plug-level CT images of the upscaling stage 3.

Figure 4B:
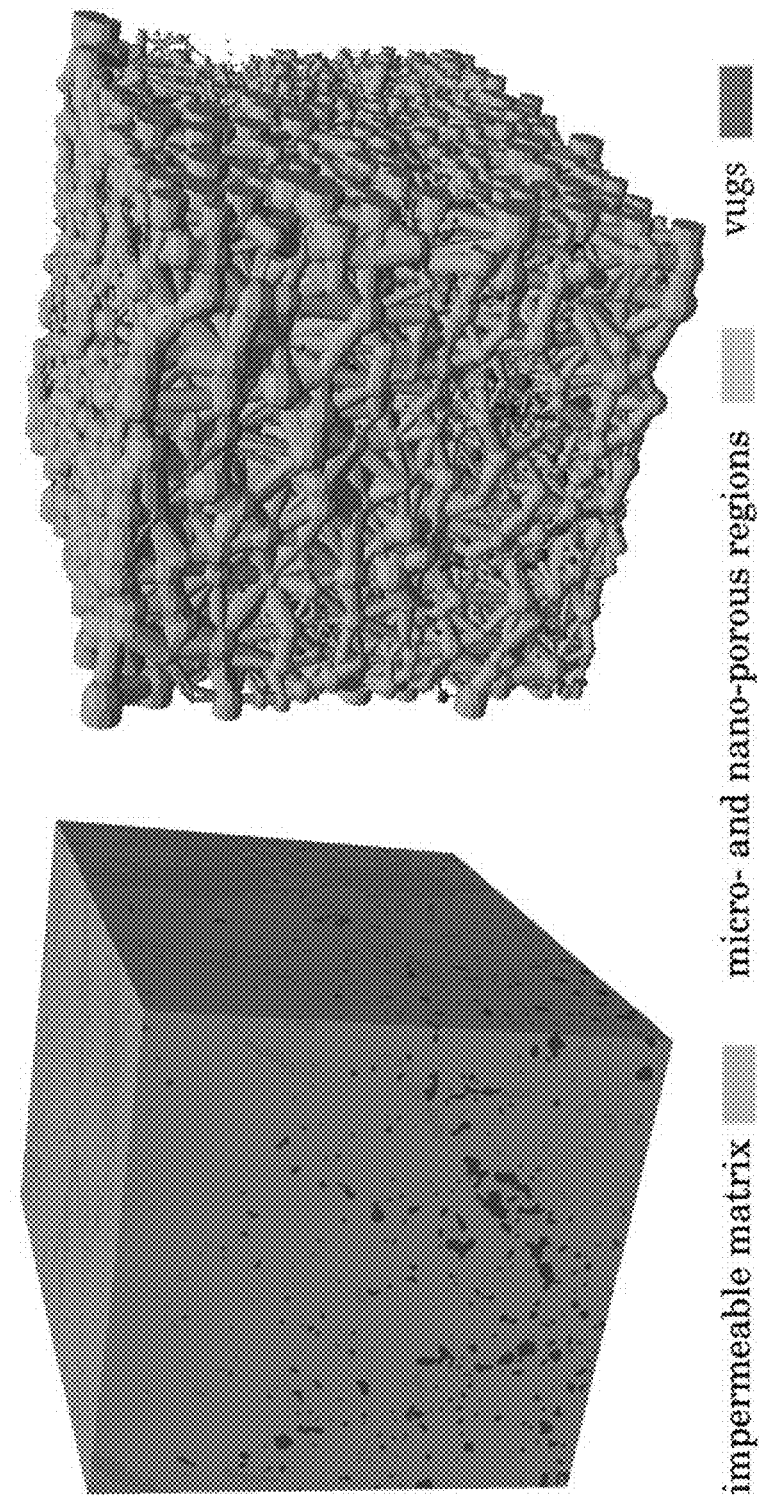
FIG. 4B illustrates the processed and segmented core-plug model and the extracted network of the upscaling stage 3.

The same network extraction code used in the upscaling stage 2 can be used to extract a network of the multi-label image, comprising vugs and micro-porosity elements. FIG. 4B illustrates the processed and segmented core-plug model and the extracted network of the upscaling stage 3, including impermeable matrices, micro- and nano-porous regions, and vugs.

Two-phase flow modeling and upscaling to the plug scale can be performed using the same flow model as in the upscaling stage 2, except that the input file is a network comprising vugs and micro-porosity (including the nano properties) elements instead of a network of micro-pores and nano-porosity elements.

The upscaling results from stage 2 can be used to describe the flow through the micro-porosity elements using a continuum (Darcy) formulation. By solving the flow equations for the combined network (referred to as the plug dual network) of vugs and micro-porosity elements, the capillary pressure curve, absolute and relative permeability, formation resistivity factor, and resistivity index can be obtained for the plug image.

Figure 4C:
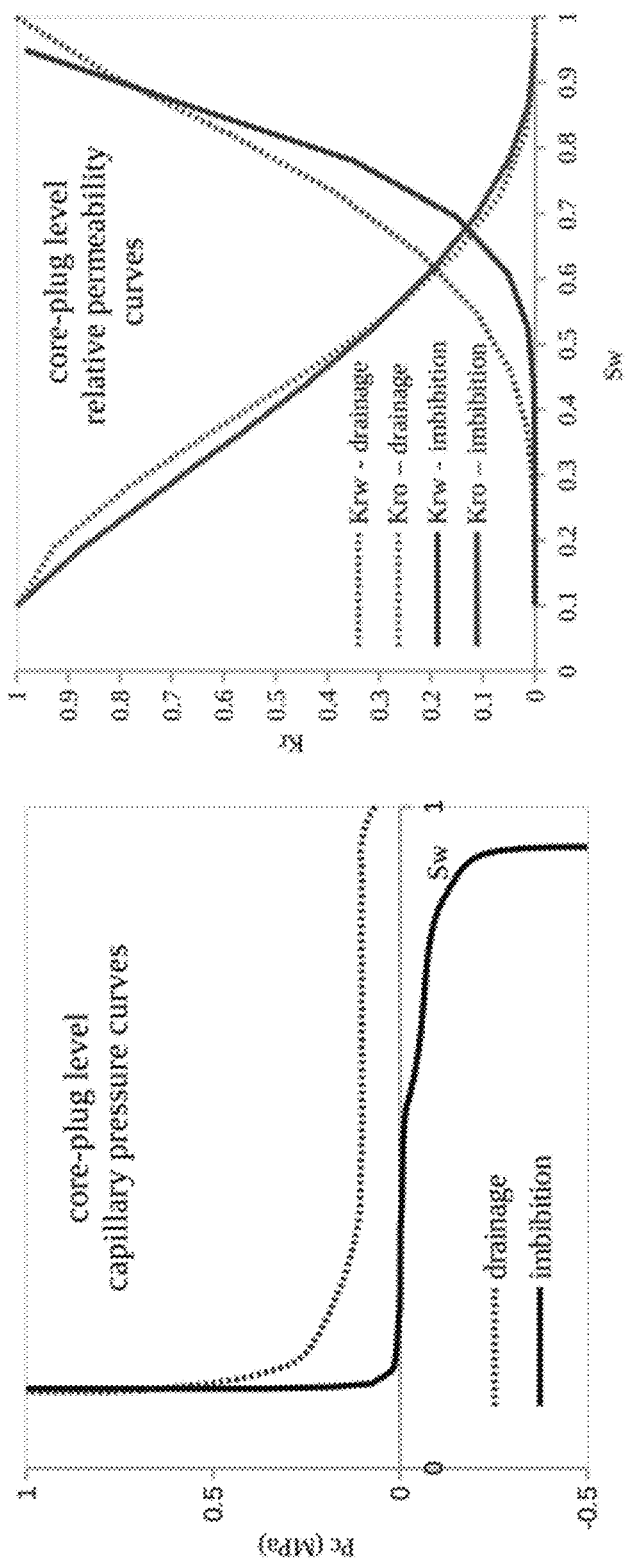
FIG. 4C illustrates the upscaling results of the upscaling stage 3.

FIG. 4C illustrates the upscaling results of the upscaling stage 3, including core-plug level capillary pressure curves for drainage and imbibition, and core-plug level relative permeability curves for drainage and imbibition.

The methods can be realized using a software or program code stored on any type of computer-readable medium or memory, such as a storage device including a disk or hard drive. The computer-readable medium may include a non-transitory computer-readable medium or memory, such as computer-readable media that store data for short periods of time like register memory, processor cache and Random Access Memory (RAM). The computer-readable medium may also include non-transitory media or memory, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, a tangible storage device, or other article of manufacture, for example.

Figure 5:
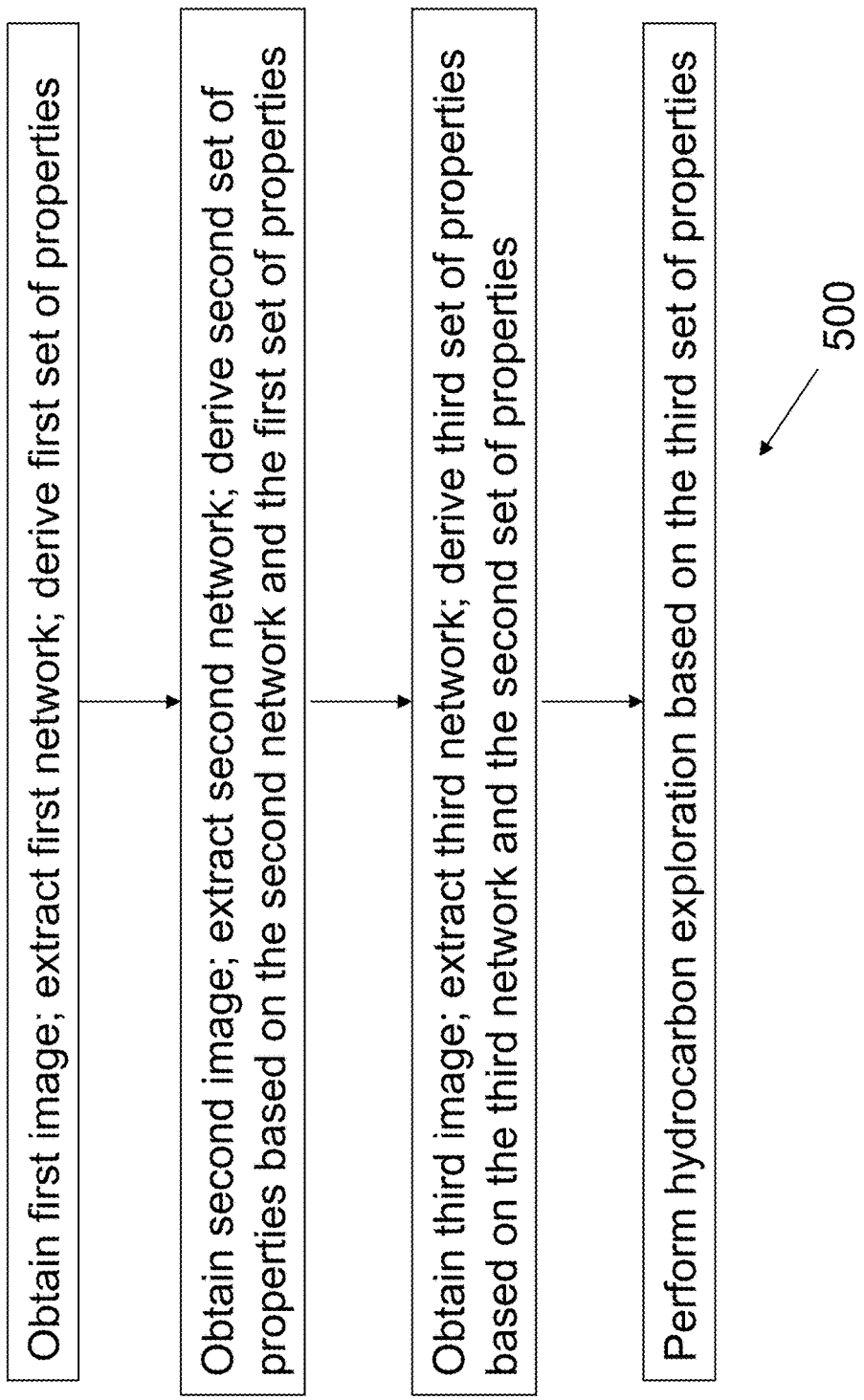
FIG. 5 is a flowchart illustrating a method according to some embodiments.

In addition, for the method 500 and other processes and methods disclosed herein, each block in FIG. 5 may represent circuitry that is wired to perform the specific logical functions in the process, and the methods can be realized using a computer system, or implemented in a larger hydrocarbon exploration system. Such a system may include a drilling subsystem as known to those of ordinary skill in the art, a measurement/logging/data collection subsystem, a telemetry subsystem, and a data processing subsystem.

Various hardware components in these systems may be known to those of ordinary skill in the art.

Alternatively, the computer system can include computer-readable medium having instructions stored thereon to perform the steps in the methods described above. Those of ordinary skill in the art will recognize that the functional blocks, methods, devices, and systems described in the present disclosure may be integrated or divided into different combinations of systems, devices, and functional blocks. Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this specification may be performed at the same time.

A "processor" includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems. Various embodiments disclosed herein can be realized via hardware and/or software, such a computer program stored on a memory. For example, a tangible, non-transitory, computer-readable storage medium having instructions stored thereon that, when executed by one or more processors, cause the one or more processors to perform operations including the steps described above.

The memory or storage medium may be any suitable data storage, memory and/or non-transitory computer-readable storage medium, including electronic storage devices such as RAM, ROM, magnetic storage device (hard disk drive or the like), flash, optical storage device (CD, DVD or the like), magnetic or optical disk, or other tangible media such as non-transitory computer-readable medium suitable for storing instructions for execution by the processor. The software instructions can also be contained in, and provided as, an electronic signal, for example in the form of software as a service (SaaS) delivered from a server (e.g., a distributed system and/or a cloud computing system).

All references in the present disclosure are incorporated by reference in their entirety. Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A computer-implemented method for deriving properties of a porous material, the method comprising:
a first stage including:
obtaining a first image of the porous material on a first scale, wherein the first image comprises a 3D image obtained from scans using physical signals;
extracting a first network of pores from the first image; and
deriving a first set of properties of the porous material using a first network flow modeling based on the first network; and
a second stage including:
obtaining a second image of the porous material on a second scale larger than the first scale;
extracting a second network of pores from the second image; and
deriving a second set of properties of the porous material using a second network flow modeling based on the second network and the first set of properties; and
applying the derived properties to hydrocarbon exploration and extraction planning.

2. The method of claim 1, further comprising:
a third stage including
obtaining a third image of the porous material on a third scale larger than the second scale;
extracting a third network of pores from the third image; and
deriving a third set of properties of the porous material using a third network flow modeling based on the third network and the second set of properties.

3. The method of claim 2, further comprising applying the third set of properties in hydrology, petroleum engineering, or environment engineering.

4. The method of claim 2, wherein the third set of properties comprise petrophysical properties and/or fluid flow data of the porous material, the method further comprising upscaling the third set of properties to a scale of reservoir modeling to thereby estimate a hydrocarbon content in the reservoir.

5. The method of claim 2, wherein:
the first scale is nano-scale;
the second scale is micro-scale; and
the third scale is macro-scale; the method further comprising:
segmenting voxels in the second scale into solid voxels, pore voxels, and voxels containing nano-scale pores.

6. The method of claim 5, wherein:
the third scale is a plug scale; and
applying a two-phase flow model with an input of a network comprising vugs and micro-porosity elements.

7. The method of claim 2, wherein the first set of parameters comprise at least one of absolute permeability (k), capillary pressure (Pc), relative permeability (kr), formation resistivity factor, or resistivity index.

8. The method of claim 2, wherein the first image comprises at least one of a CT image or an FIB-SEM image.

9. The method of claim 8, wherein the first image comprises a nano-CT X-ray image.

10. The method of claim 9, wherein the second image comprises a micro-CT X-ray image.

11. The method of claim 10, wherein the third image comprises a macro-CT X-ray image.

12. The method of claim 2, wherein the second network comprises a dual-network including both nano-scale pores and micron-scale pores.

13. The method of claim 2, wherein the porous material comprises a porous rock.

14. The method of the claim 13, wherein the porous rock comprises at least one of a carbonate reservoir rock, shale, or tight sand.

15. A non-transitory computer-readable medium having instructions stored thereon for deriving properties of a porous material, the instructions comprising:
obtaining a first image of the porous material on a first scale, wherein the first image comprises a 3D image obtained from scans using physical signals;
extracting a first network of pores from the first image; and
deriving a first set of properties of the porous material using a first network flow modeling based on the first network; and
obtaining a second image of the porous material on a second scale larger than the first scale;
extracting a second network of pores from the second image;
deriving a second set of properties of the porous material using a second network flow modeling based on the second network and the first set of properties; and
applying the derived properties to hydrocarbon exploration and extraction planning.

16. The non-transitory computer-readable medium of claim 15, wherein the instructions further comprise:
obtaining a third image of the porous material on a third scale larger than the second scale;
extracting a third network of pores from the third image; and
deriving a third set of properties of the porous material using a third network flow modeling based on the third network and the second set of properties.

17. The non-transitory computer-readable medium of claim 16, wherein the instructions further comprise applying the third set of properties in hydrology, petroleum engineering, or environment engineering.

18. The non-transitory computer-readable medium of claim 16, wherein the third set of properties comprise petrophysical properties and/or fluid flow data of the porous material, the method further comprising upscaling the third set of properties to a scale of reservoir modeling to thereby estimate a hydrocarbon content in the reservoir.

19. A computer system for deriving properties of a porous material, wherein the computer system is configured to:
obtain a first image of the porous material on a first scale, wherein the first image comprises a 3D image obtained from scans using physical signals;
extract a first network of pores from the first image;
derive a first set of properties of the porous material using a first network flow modeling based on the first network;
obtain a second image of the porous material on a second scale larger than the first scale;
extract a second network of pores from the second image;
derive a second set of properties of the porous material using a second network flow modeling based on the second network and the first set of properties;
obtain a third image of the porous material on a third scale larger than the second scale;
extract a third network of pores from the third image;
derive a third set of properties of the porous material using a third network flow modeling based on the third network and the second set of properties; and
apply the derived properties to hydrocarbon exploration and extraction planning.

20. The computer system of claim 19, wherein the computer system is further configured to display the third set of properties comprising at least one of absolute permeability (k), capillary pressure (Pc), relative permeability (kr), formation resistivity factor (FRF), or resistivity index (RI).

* * * * *